(12) United States Patent
Iwami (10) Patent No.: US 11,341,357 B2
(45) Date of Patent: May 24, 2022

(54) MEDICINE INSPECTION DEVICE, IMAGE PROCESSING DEVICE, IMAGE PROCESSING METHOD, AND PROGRAM

(71) Applicant: FUJIFILM Toyama Chemical Co., Ltd., Tokyo (JP)

(72) Inventor: Kazuchika Iwami, Ashigarakami-gun (JP)

(73) Assignee: FUJIFILM TOYAMA CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/782,943

(22) Filed: Feb. 5, 2020

(65) Prior Publication Data

US 2020/0175317 A1    Jun. 4, 2020

Related U.S. Application Data

(63) Continuation of application No. PCT/JP2018/029772, filed on Aug. 8, 2018.

(30) Foreign Application Priority Data

Aug. 31, 2017 (JP) .............................. JP2017-167652

(51) Int. Cl.
   *G06K 9/62* (2022.01)
   *G06T 7/586* (2017.01)
   (Continued)

(52) U.S. Cl.
   CPC ......... *G06K 9/6215* (2013.01); *G06K 7/1413* (2013.01); *G06T 5/00* (2013.01);
   (Continued)

(58) Field of Classification Search
   None
   See application file for complete search history.

(56) References Cited

U.S. PATENT DOCUMENTS 6,776,341 B1 * 8/2004 Sullivan .................. A61J 3/007
                                                    235/375
2006/0226234 A1 * 10/2006 Kettinger ................ B41F 17/36
                                                    235/487
(Continued)

FOREIGN PATENT DOCUMENTS

JP        2010-117331 A    5/2010
JP        2015-54115 A     3/2015
(Continued)

OTHER PUBLICATIONS

M. Bukovec, Ž. Špiclin, F. Pernuš, & B. Likar, "Automated visual inspection of imprinted pharmaceutical tablets", 18 Measurement Sci. & Tech. 2921-2930 (Aug. 2007) (Year: 2007).*

(Continued)

*Primary Examiner* — David N Werner
(74) *Attorney, Agent, or Firm* — Birch, Stewart, Kolasch & Birch, LLP.

(57) ABSTRACT

A medicine inspection device, an image processing device, an image processing method, and a program are provided that appropriately extract identification information even when the positional relationship between a printed character and an engraved mark added to a medicine is not constant. The above problem is solved by an image processing device that performs a process of enhancing a printed character portion of a medicine based on at least one image taken with a surface of the medicine being irradiated with light to generate a printed-character-enhanced image, performs a process of extracting only an engraved mark portion from a three-dimensional shape of the medicine based on at least three images taken with illumination directions of the light to the surface of the medicine different from each other to generate an engraved-mark-extracted image, and generates a (Continued)

difference image between the printed-character-enhanced image and the engraved-mark-extracted image.

11 Claims, 8 Drawing Sheets

(51) Int. Cl.
| | |
|---|---|
| *G16H 70/40* | (2018.01) |
| *G06K 7/14* | (2006.01) |
| *G06T 5/00* | (2006.01) |
| *G06T 7/00* | (2017.01) |
| *H04N 5/225* | (2006.01) |
| *G06V 10/145* | (2022.01) |
| *G06V 10/75* | (2022.01) |

(52) U.S. Cl.
CPC ............ *G06T 7/0002* (2013.01); *G06T 7/586* (2017.01); *G06V 10/145* (2022.01); *G16H 70/40* (2018.01); *H04N 5/2256* (2013.01); *G06T 2207/20224* (2013.01); *G06V 10/759* (2022.01)

(56) References Cited

U.S. PATENT DOCUMENTS

| | | | | |
|---|---|---|---|---|
| 2008/0219503 A1* | 9/2008 | Di Venuto | ........... | G06K 9/6857 382/103 |
| 2009/0063056 A1* | 3/2009 | Chang | ................ | A63B 71/0605 702/19 |
| 2011/0091068 A1* | 4/2011 | Stuck | ................... | G03H 1/0011 382/103 |
| 2011/0244919 A1* | 10/2011 | Aller | ................. | G06Q 30/0281 455/556.1 |
| 2012/0243797 A1* | 9/2012 | Di Venuto Dayer | ........................ G06K 9/00577 382/218 |
| 2012/0290619 A1* | 11/2012 | DeLise, Jr. | ........ | G06K 9/00671 707/776 |
| 2012/0330684 A1* | 12/2012 | Jacobs | ..................... | H04N 7/18 705/3 |
| 2013/0127959 A1* | 5/2013 | Hanina | .................. | G06K 1/121 347/101 |
| 2014/0009262 A1* | 1/2014 | Robertson | .............. | A61B 5/053 340/5.52 |
| 2014/0306010 A1* | 10/2014 | Prokop | ................ | G06K 9/6202 235/440 |
| 2015/0016664 A1* | 1/2015 | Rodriguez | ............. | G07D 7/005 382/100 |
| 2016/0203291 A1 | 7/2016 | Ebata | | |
| 2016/0210524 A1 | 7/2016 | Hasegawa | | |
| 2017/0264867 A1 | 9/2017 | Amano et al. | | |
| 2017/0305589 A1* | 10/2017 | Yuyama | .................. | B65B 35/26 |
| 2018/0177682 A1* | 6/2018 | Tanaka | .................. | A61J 7/0084 |
| 2019/0050660 A1* | 2/2019 | Iwami | .................. | G06T 7/0012 |
| 2020/0175318 A1* | 6/2020 | Yokouchi | .................. | G06T 5/50 |
| 2020/0175319 A1* | 6/2020 | Yokouchi | .................. | G06T 7/13 |

FOREIGN PATENT DOCUMENTS

| | | |
|---|---|---|
| JP | 2015-65978 A | 4/2015 |
| WO | WO 2015/152225 A1 | 10/2015 |
| WO | WO 2017/119276 A1 | 7/2017 |

OTHER PUBLICATIONS

International Preliminary Report on Patentability and Written Opinion of the International Searching Authority with an English translation (forms PCT/IB/373 and PCT/ISA/237), dated Mar. 3, 2020, for corresponding International Application No. PCT/JP2018/029772.

International Search Report (form PCT/ISA/210), dated Nov. 13, 2018, for corresponding International Application No. PCT/JP2018/029772, with an English translation.

Extended European Search Report dated Aug. 7, 2020 for Application No. 18850543.2.

Podrekar et al., "Model based visual inspection of pharmaceutical tablets with photometric stereo", 2017 Fifteenth IAPR International Conference on Machine Vision Applications (MVA) Nagoya University, Nagoya, Japan, May 8-12, 2017, pp. 133-136.

* cited by examiner

MEDICINE INSPECTION DEVICE, IMAGE PROCESSING DEVICE, IMAGE PROCESSING METHOD, AND PROGRAM

CROSS-REFERENCE TO RELATED APPLICATIONS

The present application is a Continuation of PCT International Application No. PCT/JP2018/029772 filed on Aug. 8, 2018 claiming priority under 35 U.S.C § 119(a) to Japanese Patent Application No. 2017-167652 filed on Aug. 31, 2017. Each of the above applications is hereby expressly incorporated by reference, in its entirety, into the present application.

BACKGROUND OF THE INVENTION

1. Field of the Invention

The present invention relates to a medicine inspection device, an image processing device, an image processing method and a program, and in particular, to a medicine inspection (audit) device, an image processing device, an image processing method and a program that identify the kind of a medicine from an image obtained by imaging the medicine.

2. Description of the Related Art

When a pharmacist or the like prepares medicines and packages the medicines in a divided manner according to a prescription in a hospital or a pharmacy, he or she is obliged to inspect whether or not the medicines are packaged in conformity with the prescription after the packaging. Until now, for the sake of reducing artificial inspection errors in the inspection operation or load in the inspection operation, various techniques have been contemplated. Among those techniques, a technique has been known that collates an image obtained by imaging a medicine with an image of a medicine preliminarily registered in a server or the like, and identifies a kind of the imaged medicine.

As a typical technical method of collating images with each other, there is a collating method of calculating similarity by a correlation operation on each image to perform collation. However, in a case where this method is performed for identification information added to medicines, if the identification information added to the medicines are similar to each other or the medicines have cleavage lines, the similarity becomes high even between images of different medicines, and a collating device sometimes outputs an erroneous determination result.

To address such a problem, Japanese Patent Application Laid-Open No. 2015-065978 (hereinafter referred to as "PTL 1") discloses a technique for a medicine collating device that calculates similarities of partial images in divided areas of a registered image and a collation target image (image to be collated) for corresponding divided areas, and determines whether or not the medicine indicated by the registered image is the same kind as the medicine indicated by the collation target image based on the lowest similarity among the calculated similarities for the divided areas, in which an image processing unit extracts a cleavage line and a similarity calculating unit sets divided areas such that the cleavage line is not included in partial images in a case where the registered image including a cleavage line on a surface of a medicine is obtained.

According to this device, even in a case where medicines having similar identification information or cleavage lines are collated with each other, correct collation can be performed.

CITATION LIST

PTL 1: Japanese Patent Application Laid-Open No. 2015-065978

SUMMARY OF THE INVENTION

However, the technique described in PTL 1 assumes that positional relationship between a printed character and an engraved mark (cleavage line) added to the medicine is constant (uniform). Accordingly, there is a problem in that if the positional relationship between the printed character and the engraved mark is not constant, the identification information cannot be extracted, and collation cannot appropriately be performed.

The present invention has been made in view of such situations, and aims to provide a medicine inspection device, an image processing device, an image processing method and a program that appropriately extract identification information even in a case where the positional relationship between a printed character and an engraved mark added to a medicine is not constant (uniform).

To achieve the above object, an aspect of an image processing device includes: a first image obtaining unit configured to obtain at least one taken image of a medicine, the taken image being taken with a surface of the medicine being irradiated with light; a first image processing unit configured to perform a process of enhancing a printed character portion of the medicine based on the at least one taken image, and generate a printed-character-enhanced image; a second image obtaining unit configured to obtain at least three taken images of the medicine, the images being taken with illumination directions of light to the surface of the medicine different from each other; a second image processing unit configured to perform a process of extracting only an engraved mark portion from a three-dimensional shape of the medicine based on the at least three taken images, and generate an engraved-mark-extracted image; and a difference image generating unit configured to generate a difference image between the printed-character-enhanced image and the engraved-mark-extracted image.

According to this aspect, the image processing device generates the difference image between the printed-character-enhanced image generated based on at least one taken image of the medicine with the surface of the medicine being irradiated with light, and the engraved-mark-extracted image generated based on at least three taken images of the medicine with the illumination directions of light to the surface of the medicine different from each other. Therefore, even in a case where the positional relationship between the engraved mark and the printed character added to the medicine is not constant, the identification information can be appropriately extracted.

Preferably, the second image processing unit includes: a three-dimensional information obtaining unit configured to obtain three-dimensional information on the surface of the medicine by photometric stereo based on at least three taken images; and a curvature image generating unit configured to generate a curvature image that represents a curvature of a local area of the surface of the medicine based on the obtained three-dimensional information, and the generated curvature image is adopted as the engraved-mark-extracted image. Accordingly, the engraved-mark-extracted image can be appropriately generated. Further, the second image processing unit may normalize at least three taken images with the average signal value.

Preferably, the first image processing unit performs a process of removing a low-frequency component from at least one taken image. Accordingly, the printed-character-enhanced image can be appropriately generated.

To achieve the above object, an aspect of a medicine inspection device includes: a stage on which a medicine is placed; an irradiating unit configured to include at least three light sources that irradiate a surface of the medicine placed on the stage with light in a plurality of illumination directions different from each other; an imaging unit configured to image the medicine; a first imaging control unit configured to control the irradiating unit and the imaging unit to obtain at least one taken image of the medicine, the image being taken with the surface of the medicine being irradiated with light; a first image processing unit configured to perform a process of enhancing a printed character portion of the medicine based on at least one taken image, and generate a printed-character-enhanced image; a second imaging control unit configured to control the irradiating unit and the imaging unit to obtain at least three taken images of the medicine, the images being taken with illumination directions of the light to the surface of the medicine different from each other; a second image processing unit configured to perform a process of extracting only an engraved mark portion from a three-dimensional shape of the medicine based on at least three taken images, and generate an engraved-mark-extracted image; and a difference image generating unit configured to generate a difference image between the printed-character-enhanced image and the engraved-mark-extracted image.

According to this aspect, the medicine inspection device generates the difference image between the printed-character-enhanced image generated based on at least one taken image of the medicine with the surface of the medicine being irradiated with light, and the engraved-mark-extracted image generated based on at least three taken images of the medicine with the illumination directions of light to the surface of the medicine being different from each other. Accordingly, even in case where the positional relationship between the engraved mark and the printed character added to the medicine is not constant, the identification information can be appropriately extracted.

Preferably, the medicine inspection device further includes: a prescription information obtaining unit configured to obtain prescription information; a master image obtaining unit configured to obtain a master image of a medicine to be dispensed based on the prescription information; and a determining unit configured to collate the master image with the generated difference image, and determine whether or not the medicine to be dispensed is identical to the medicine placed on the stage. Accordingly, it can be appropriately determined whether the medicine to be dispensed is identical to the medicine placed on the stage or not.

Preferably, the medicine inspection device further include: a region-of-interest setting unit configured to set a region of interest in an image of the medicine; and a template generating unit configured to generate a template from the master image in conformity with the set region of interest, and the determining unit collates the region of interest of the difference image with the template. Accordingly, it can be appropriately determined whether the medicine to be dispensed is identical to the medicine placed on the stage or not.

Preferably, a plurality of medicines packaged into a divided bag are placed on the stage. This mode is applicable to a plurality of medicines packaged in a divided bag.

Preferably, the irradiating unit includes a first light source configured to emit light in a first direction, a second light source configured to emit light in a second direction, a third light source configured to emit light in a third direction, and a fourth light source configured to emit light in a fourth direction, and the second direction is a direction opposite to the first direction in plan view of the surface, the third direction is a direction orthogonal to the first direction in plan view of the surface, and the fourth direction is a direction opposite to the third direction in plan view of the surface. Accordingly, it is possible to appropriately obtain at least three taken images of the medicine which are taken with illumination directions of the light to the surface of the medicine being different from each other.

Preferably, the first imaging control unit causes the first light source, the second light source, the third light source and the fourth light source to irradiate the surface of the medicine with light. Accordingly, it is possible to appropriately obtain at least one taken image of the medicine which is taken with the surface of the medicine being irradiated with light.

To achieve the above object, an aspect of an image processing method includes: a first image obtaining step of obtaining at least one taken image of a medicine, the image being taken with a surface of the medicine being irradiated with light; a first image processing step of performing a process of enhancing a printed character portion of the medicine based on at least one taken image, and generate a printed-character-enhanced image; a second image obtaining step of obtaining at least three taken images of the medicine, the images being taken with illumination directions of the light to the surface of the medicine different from each other; a second image processing step of performing a process of extracting only an engraved mark portion from a three-dimensional shape of the medicine based on at least three taken images, and generating an engraved-mark-extracted image; and a difference image generating step of generating a difference image between the printed-character-enhanced image and the engraved-mark-extracted image.

According to this aspect, the image processing method generates the difference image between the printed-character-enhanced image generated based on at least one taken image of the medicine with the surface of the medicine being irradiated with light, and the engraved-mark-extracted image generated based on at least three taken images of the medicine with the illumination directions of light to the surface of the medicine different from each other. Accordingly, even in a case where the positional relationship between the engraved mark and the printed character added to the medicine is not constant, the identification information can be appropriately extracted.

To achieve the above object, an aspect of a program causes a computer to execute: a first image obtaining function of obtaining at least one taken image of a medicine, the image being taken with a surface of the medicine being irradiated with light; a first image processing function of performing a process of enhancing a printed character portion of the medicine based on at least one taken image, and generate a printed-character-enhanced image; a second image obtaining function of obtaining at least three taken images of the medicine, the images being taken with illumination directions of the light to the surface of the medicine different from each other; a second image processing function of performing a process of extracting only an engraved mark portion from a three-dimensional shape of the medicine based on at least three taken images, and generating an engraved-mark-extracted image; and a difference image generating function of generating a difference image between the printed-character-enhanced image and the engraved-mark-extracted image.

According to this aspect, the program causes the computer to generate the difference image between the printed-character-enhanced image generated based on at least one taken image of the medicine with the surface of the medicine being irradiated with light, and the engraved-mark-extracted image generated based on at least three taken images of the medicine with the illumination directions of light to the surface of the medicine being different from each other. Accordingly, even in a case where the positional relationship between the engraved mark and the printed character added to the medicine is not constant, the identification information can be appropriately extracted.

According to the present invention, the identification information can be appropriately extracted even in a case where the positional relationship between the engraved mark and the printed character added to the medicine is not constant (uniform).

DESCRIPTION OF THE PREFERRED EMBODIMENTS

Hereinafter, referring to the accompanying drawings, preferred embodiments of the present invention are described in detail.

[Tablet to which Identification Information has been Added by Character Printing and Mark Engraving]

Figure 1:
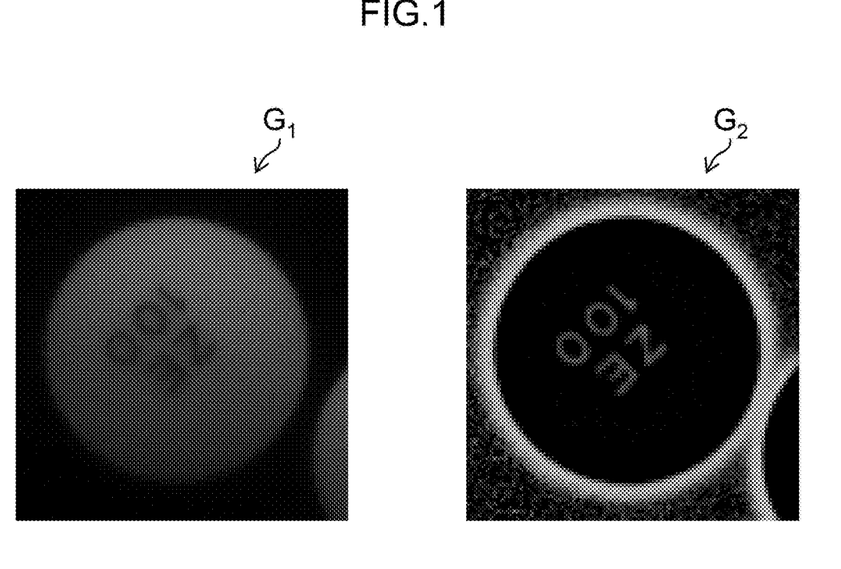
FIG. 1 shows examples of a taken image of a tablet to which identification information has been added by character printing and of a printed-character-enhanced image.

An image $G_1$ shown in FIG. 1 is an example of a taken image of a tablet (example of medicine) to which identification information has been added by character printing. In many cases, illumination irregularity and shape irregularity have a low frequency band compared to a printed character portion. Accordingly, in order to extract identification information, it is preferable to perform a process of reducing the illumination irregularity and shape irregularity which are other than the printed character portion. An image $G_2$ shown in FIG. 1 is an example of an image obtained by applying the process of reducing the illumination irregularity and shape irregularity to the image $G_1$. As described above, by obtaining the image where the printed character portion has been extracted, a medicine to be dispensed can be appropriately collated with a master image.

Figure 2:
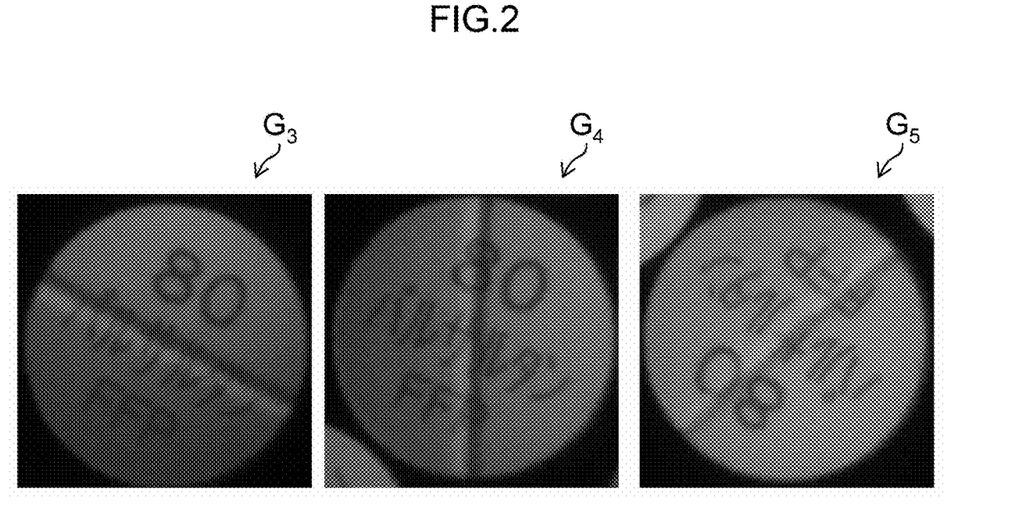
FIG. 2 shows examples of taken images of tablets each of which has identification information added by character printing and mark engraving.

An image $G_3$, an image $G_4$ and an image $G_5$ shown in FIG. 2 are examples of taken images of tablets each of which has identification information added by character printing and mark engraving (cleavage line). These images show tablets of the same kind. However, as shown in FIG. 2, these images have positional relationship between the printed characters and the engraved mark different from each other, and the positional relationship is not constant (uniform).

Figure 3:
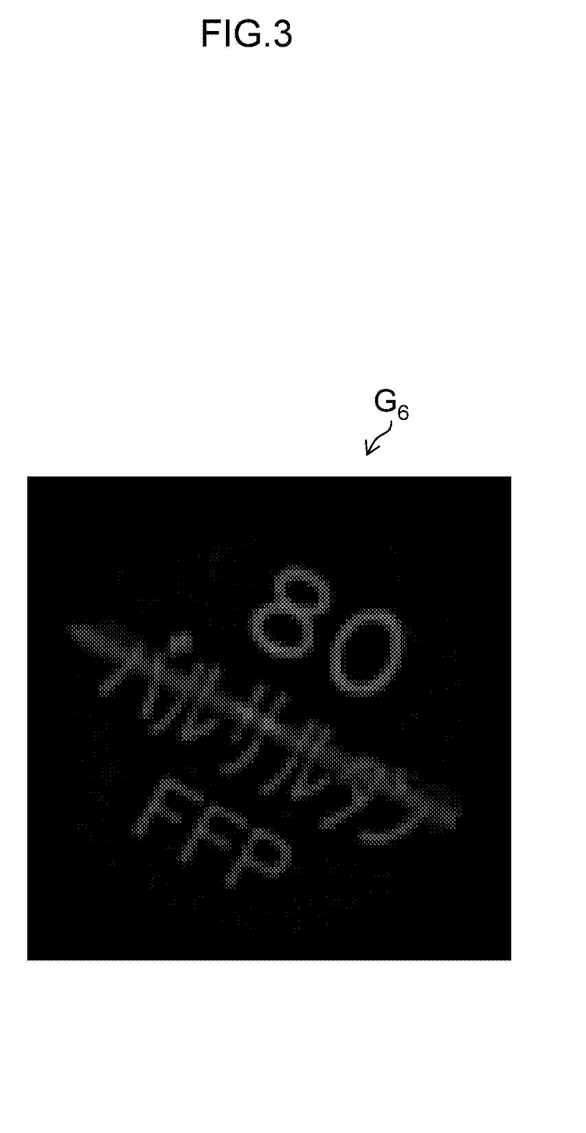
FIG. 3 shows an example of a printed-character-enhanced image of a tablet to which identification information has been added by character printing and mark engraving.

An image $G_6$ shown in FIG. 3 is an example of an image obtained by applying the process of reducing the illumination irregularity and shape irregularity to the image $G_3$. As shown in FIG. 3, in the image $G_6$, the printed character portion and the engraved mark portion are extracted. In a case where the positional relationship between the printed characters and the engraved mark is not constant, if the image from which the printed character portion and the engraved mark portion have been extracted is collated with the master image, the engraved mark portion deteriorates the collation accuracy.

The medicine inspection device according to this embodiment removes the engraved mark portion serving as a cause of reducing the similarity and enhances only the printed character portion to appropriately extract the identification information even when the positional relationship between the engraved mark portion and the printed character portion added to the medicine is not constant.

Note that addition by mark engraving means that the identification information is formed by forming a groove that is a depressed area on a surface of a medicine. The groove is not limited to what has been formed by scraping the surface. Alternatively, the groove may be what has been formed by pressing the surface. The engraved mark may include what is not accompanied by an identification function, such as a cleavage line.

Addition by character printing means that the identification information is formed by adding edible ink or the like through contact or noncontact on a surface of tablet. Here, addition by character printing has the same meaning as addition by printing.

[Configuration of Medicine Inspection Device]

Figure 4:
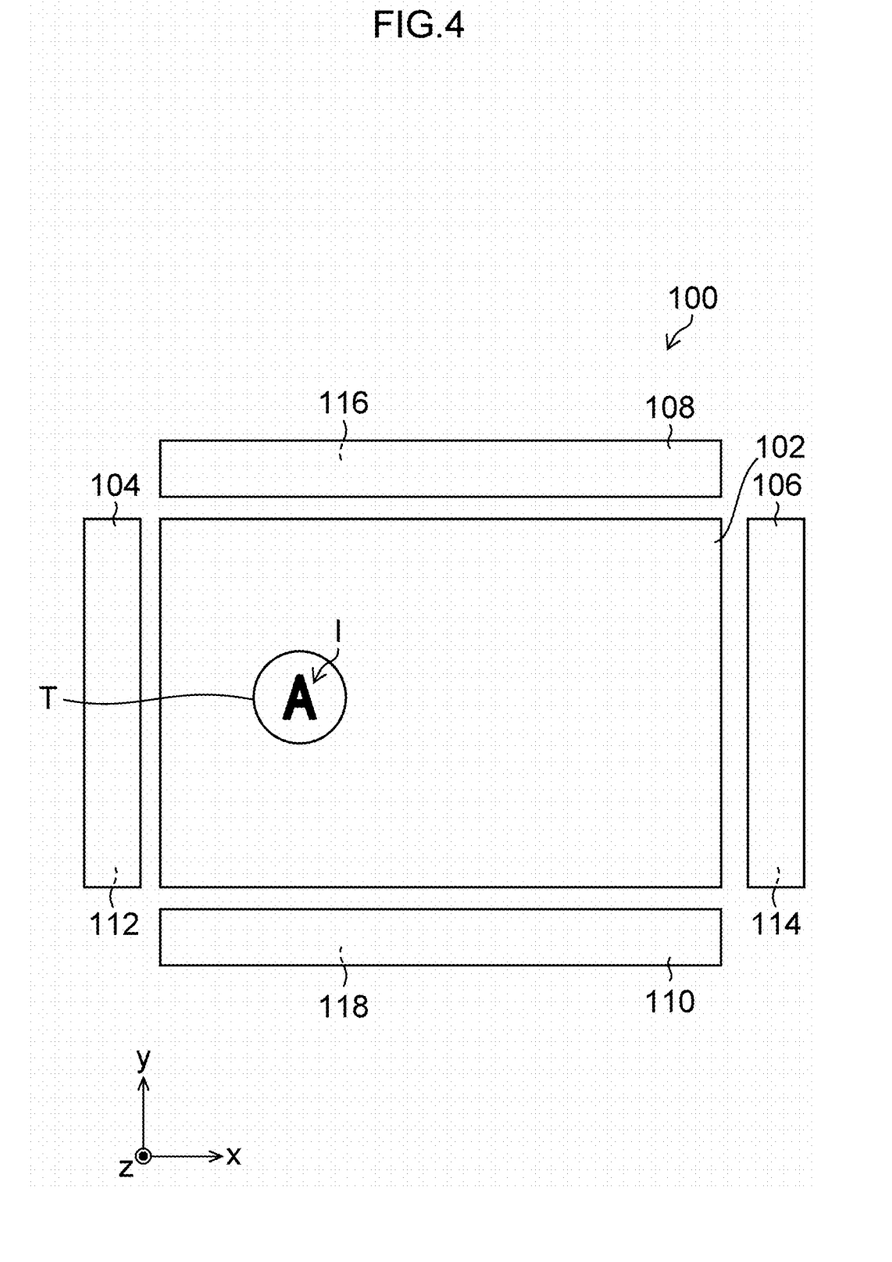
FIG. 4 is a top view of a medicine inspection device.
Figure 5:
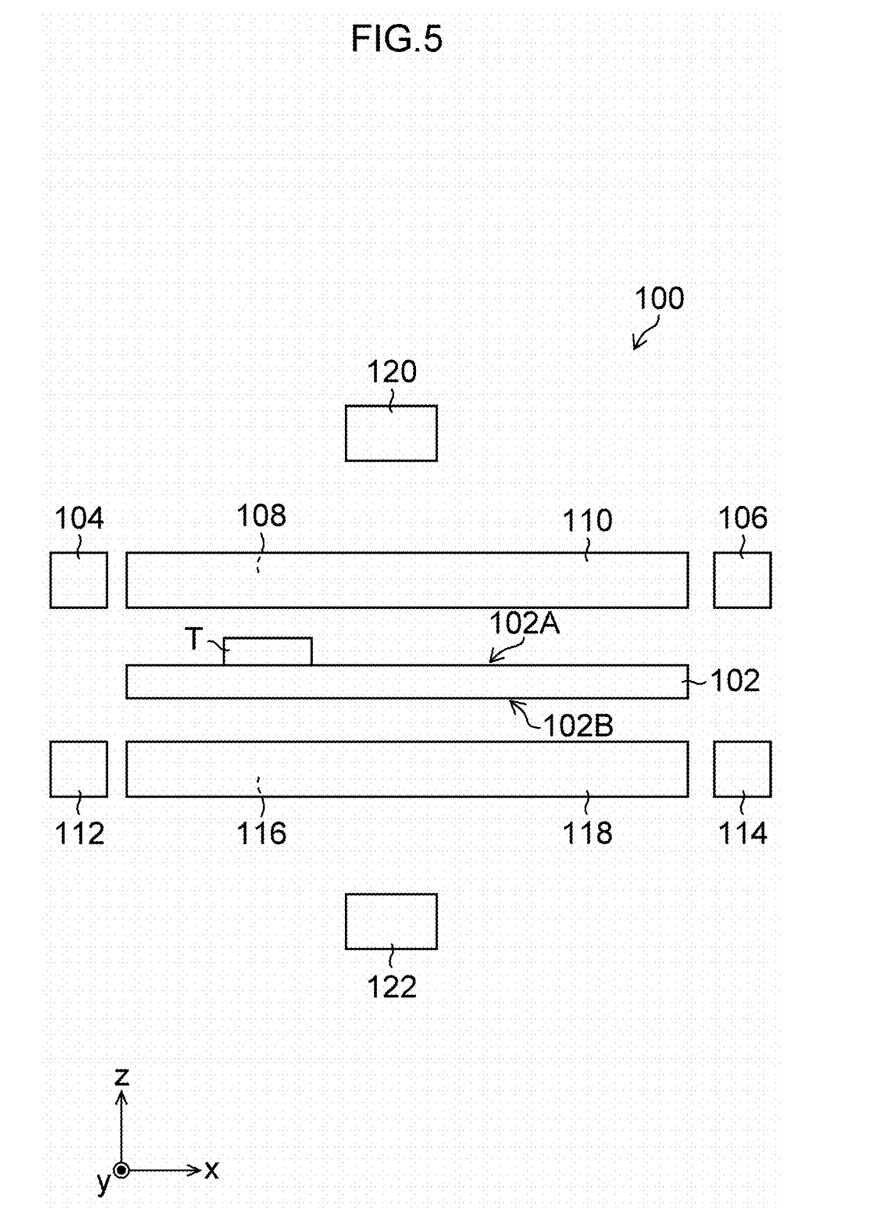
FIG. 5 is a side view of the medicine inspection device.

FIG. 4 is a top view of a medicine inspection device 100 according to this embodiment. FIG. 5 is a side view of the medicine inspection device 100.

As shown in FIGS. 4 and 5, the medicine inspection device 100 includes a stage 102, a first light source 104, a second light source 106, a third light source 108, a fourth light source 110, a fifth light source 112, a sixth light source 114, a seventh light source 116, an eighth light source 118, a camera 120 and a camera 122. Note that in FIG. 4, illustration of the camera 120 and the camera 122 is omitted.

The stage 102 is a plate-shaped member that has a mounting surface 102A and a rear surface 102B, which are parallel to the xy plane (horizontal plane). The stage 102 is made of a material having light transparency. Here, the stage 102 has sizes of 130 mm in the x-axis direction, and 80 mm in the y-axis direction. A tablet T is placed on the mounting surface 102A of the stage 102. As for the surfaces of the tablet T, a surface in contact with the mounting surface 102A is assumed as a lower surface, and an opposite surface of the lower surface is assumed as an upper surface. Identification information I on the tablet T is added by mark engraving or character printing on at least one of the upper surface and the lower surface of the tablet T. Here, the tablet T is not packaged in a divided bag. Alternatively, the tablet T may be placed in a state where the tablet T is packaged in a transparent or translucent divided bag. Multiple tablets may be packaged in the divided bag. Strip package may be configured by divided bags which are continuously connected. Further alternatively, the divided bag may be supported in a manner that can be imaged without providing the stage 102.

Each of the first light source 104, the second light source 106, the third light source 108, the fourth light source 110, the fifth light source 112, the sixth light source 114, the seventh light source 116, and the eighth light source 118 is a bar-shaped (linear) LED (Light Emitting Diode) light source. The first light source 104, the second light source 106, the third light source 108, the fourth light source 110, the fifth light source 112, the sixth light source 114, the seventh light source 116, and the eighth light source 118 are supported by a supporting unit, not shown. Each of the light sources emits illumination light that is visible light toward the stage 102 in a direction inclined from the z-axis direction. Here, when turned on, the first light source 104, the second light source 106, the third light source 108, the fourth light source 110, the fifth light source 112, the sixth light source 114, the seventh light source 116 and the eighth light source 118 have the same illuminance.

The first light source 104 is disposed in parallel to the y-axis direction at a position that is apart from the stage 102 by a certain amount in one side (upper side in FIG. 5) in the z-axis direction and is one side (left side in FIG. 4) of the mounting surface 102A in the x-axis direction. The first light source 104 emits illumination light in a first direction toward the stage 102.

The second light source 106 is disposed in parallel to the y-axis direction at a position that is apart from the stage 102 by a certain amount on the one side in the z-axis direction and is on the other side (right side in FIG. 4) in the x-axis direction. The second light source 106 emits illumination light in a second direction toward the stage 102. The second direction is a direction opposite to the first direction in xy-plan view (an example of plan view of the surface).

The third light source 108 is disposed in parallel to the x-axis direction at a position that is apart from the stage 102 by a certain amount on the one side in the z-axis direction and is on the one side (upper side in FIG. 4) in the y-axis direction. The third light source 108 emits illumination light in a third direction toward the stage 102. The third direction is a direction orthogonal to the first direction in the xy-plan view.

The fourth light source 110 is disposed in parallel to the x-axis direction at a position that is apart from the stage 102 by a certain amount on the one side in the z-axis direction and is on the other side (lower side in FIG. 4) in the y-axis direction. The fourth light source 110 emits illumination light in a fourth direction toward the stage 102. The fourth direction is a direction opposite to the third direction in the xy-plan view.

The fifth light source 112 is disposed in parallel to the y-axis direction at a position that is apart from the stage 102 by a certain amount on the other side (lower side in FIG. 5) in the z-axis direction and is on the one side in the x-axis direction. The fifth light source 112 emits illumination light in a fifth direction toward the stage 102. The fifth direction is the same direction as the first direction in the xy-plan view.

The sixth light source 114 is disposed in parallel to the y-axis direction at a position that is apart from the stage 102 by a certain amount on the other side in the z-axis direction and is on the other side in the x-axis direction. The sixth light source 114 emits illumination light in a sixth direction toward the stage 102. The sixth direction is a direction opposite to the fifth direction in the xy-plan view.

The seventh light source 116 is disposed in parallel to the x-axis direction at a position that is apart from the stage 102 by a certain amount on the other side in the z-axis direction and is on the one side in the y-axis direction. The seventh light source 116 emits illumination light in a seventh direction toward the stage 102. The seventh direction is a direction orthogonal to the fifth direction in the xy-plan view.

The eighth light source 118 is disposed in parallel to the x-axis direction at a position that is apart from the stage 102 by a certain amount on the other side in the z-axis direction and is on the other side in the y-axis direction. The eighth light source 118 emits illumination light in an eighth direction toward the stage 102. The eighth direction is a direction opposite to the seventh direction in the xy-plan view.

The camera 120 and the camera 122 (example of imaging unit) are imaging devices that take color images of visible light, and are supported by a supporting unit, not shown. The camera 120 and the camera 122 each include lenses and an imaging element.

The camera 120 is provided at a position apart from the stage 102 by a certain amount on one side in the z-axis direction. The camera 120 is disposed to face the mounting surface 102A, with the optical axis being in parallel to the z-axis direction. The camera 122 is provided at a position apart from the stage 102 by a certain amount on the other side in the z-axis direction. The camera 122 is disposed to face the rear surface 102B, with the optical axis being in parallel to the z-axis direction. The optical axis of the camera 120 and the optical axis of the camera 122 are opposite to each other via the stage 102.

Figure 6:
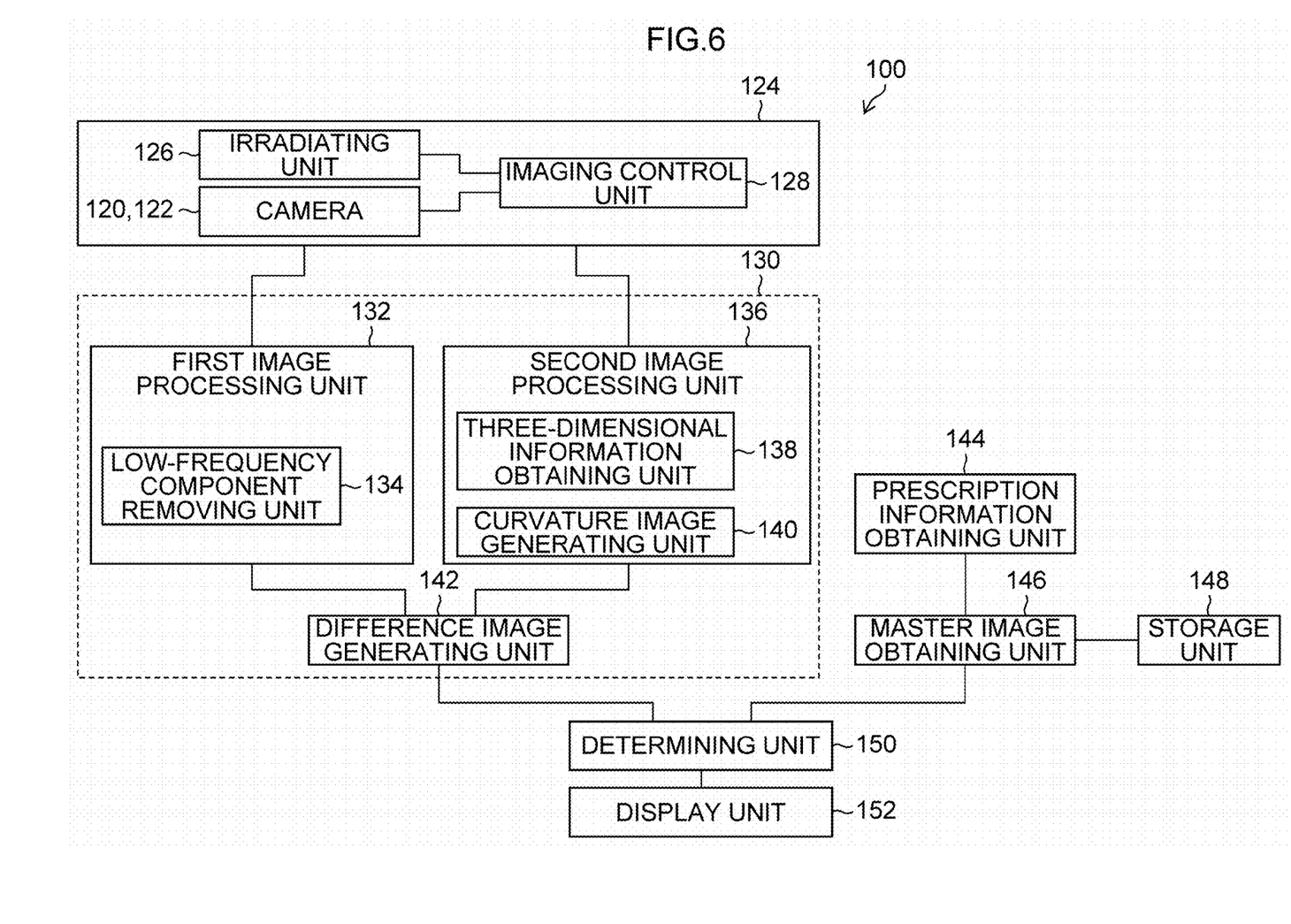
FIG. 6 is a block diagram showing an internal configuration of the medicine inspection device.

FIG. 6 is a block diagram showing an internal configuration of the medicine inspection device 100. The medicine inspection device 100 includes an obtaining unit 124, an image processing device 130, a prescription information obtaining unit 144, a master image obtaining unit 146, a storage unit 148, a determining unit 150 and a display unit 152.

The obtaining unit 124 (example of first image obtaining unit, and example of second image obtaining unit) includes an irradiating unit 126 and an imaging control unit 128, in addition to the camera 120 and the camera 122 described above.

The irradiating unit 126 includes a plurality of light sources. Here, the irradiating unit 126 includes the first light source 104, the second light source 106, the third light source 108, the fourth light source 110, the fifth light source 112, the sixth light source 114, the seventh light source 116, and the eighth light source 118, which are described above.

The imaging control unit 128 (example of first imaging control unit, and example of second imaging control unit) controls turning on and off of each light source of the irradiating unit 126.

The imaging control unit 128 controls the camera 120 and the camera 122. According to control by the imaging control unit 128, the camera 120 and the camera 122 each image the tablet T (tablets T) whose surface is irradiated with light by the plurality of light sources, and. Accordingly, the obtaining unit 124 obtains a plurality of taken images.

Note that the obtaining unit 124 may be configured to include a communication interface for communication with an external device, such as a computer, thereby obtaining a plurality of images of the tablet T from the external device.

The image processing device 130 includes a first image processing unit 132, a second image processing unit 136 and a difference image generating unit 142.

The first image processing unit 132 performs a process of enhancing the printed character portion of a medicine based on at least one taken image, and generates a printed-character-enhanced image. The first image processing unit 132 includes a low-frequency component removing unit 134. The low-frequency component removing unit 134 performs a process of removing a low-frequency component from at least one taken image.

The second image processing unit 136 performs a process of extracting only the engraved mark portion from the three-dimensional shape of the tablet based on at least three taken images, and generates an engraved-mark-extracted image. The second image processing unit 136 includes a three-dimensional information obtaining unit 138, and a curvature image generating unit 140.

The three-dimensional information obtaining unit 138 obtains three-dimensional information on the surface of the tablet by photometric stereo based on at least three taken images. The curvature image generating unit 140 generates a curvature image that represents a curvature of a local area in the surface of the tablet (tablets) based on the three-dimensional information.

The difference image generating unit 142 generates a difference image between the printed-character-enhanced image and the engraved-mark-extracted image.

The prescription information obtaining unit 144 includes, for example, a prescription reader, not shown, and reads a prescription and obtains prescription information. For example, through OCR (Optical Character Recognition), information on a patient's name, prescribed medicines, medicines' quantities and the like is read from the prescription written on a paper sheet. In a case where a bar code or the like indicating information pertaining to the prescribed medicines is recorded on the prescription, the information on the prescribed medicines, their quantities and the like may be read from the bar code. Alternatively, a user may read the prescription and input the prescription information through an input device such as a keyboard, not shown.

The master image obtaining unit 146 obtains master images of medicine (medicines) to be dispensed from the storage unit 148 based on the prescription information obtained by the prescription information obtaining unit 144.

The storage unit 148 may be a non-transitory recording medium, such as a CD (Compact Disk), a DVD (Digital Versatile Disk), a hard disk, and various semiconductor memories. The storage unit 148 stores the prescription information, the master images, the taken images taken by the camera 120 and the camera 122, or processed taken images to which image processing has been applied, in association with each other.

The determining unit 150 collates the master images obtained by the master image obtaining unit 146 and the difference image generated by the difference image generating unit 142 with each other, and determines whether or not the medicine to be dispensed is the same as the medicine placed on the stage 102.

The display unit 152 includes a monitor, not shown, and displays the prescription information obtained from the prescription information obtaining unit 144, the taken images of the packaged medicine (medicines), the master images stored in the storage unit 148 and the like. Furthermore, the display unit 152 displays a determination result of the determining unit 150.

[Image Processing Method]

Figure 7:
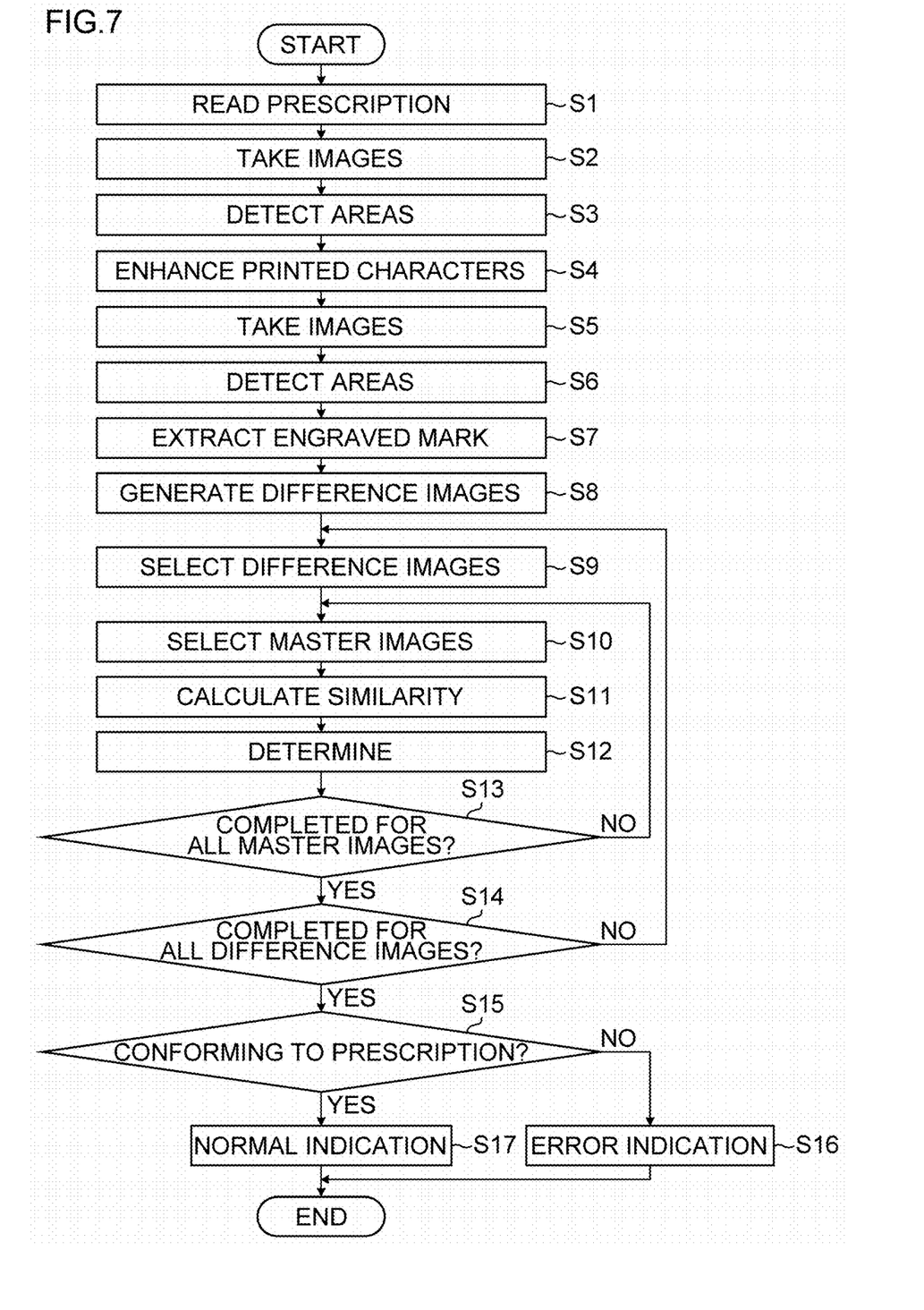
FIG. 7 is a flowchart showing an example of processes of an image processing method.

An image processing method according to this embodiment is described. FIG. 7 is a flowchart showing an example of processes of the image processing method.

In step S1, the prescription information obtaining unit 144 reads the prescription and obtains the prescription information. The prescription information obtaining unit 144 may read prescription information preliminarily stored in the storage unit 148.

In step S2 (example of first image obtaining step, example of first image obtaining function), the imaging control unit 128 turns on all of the first light source 104, the second light source 106, the third light source 108 and the fourth light source 110 disposed in one side of the z-axis direction, and the camera 120 images the tablet T in a state where the surface of the tablet is irradiated with light. Accordingly, the obtaining unit 124 obtains at least one taken image of the upper surface of the tablet T, with the upper surface of the tablet T being sufficiently illuminated.

The imaging control unit 128 causes the camera 122 to image the tablet T in a state where all of the fifth light source 112, the sixth light source 114, the seventh light source 116 and the eighth light source 118 disposed in the other side of the z-axis direction are turned on. Accordingly, the obtaining unit 124 obtains at least one taken image of the lower surface of the tablet T, with the lower surface of the tablet T being sufficiently illuminated.

In step S3, the first image processing unit 132 detects tablet areas (medicine areas) in each of which the tablet T is imaged, from the taken images obtained in step S2. When a plurality of tablets are placed on the stage 102, a plurality of tablet areas are detected from each taken image. By detecting the tablet areas, areas to which image processing in the subsequent steps is to be applied can be limited, which can reduce the time required for image processing. Here, for tablet areas of the same tablet, a tablet area of the upper surface of the tablet T detected from the taken image of the camera 120 and a tablet area of the lower surface of the tablet T detected from the taken image of the camera 122 are detected as a pair of tablet areas of the same tablet in association with each other. The image $G_3$ shown in FIG. 2 is an example of the tablet area.

In step S4 (example of first image processing step, example of first image processing function), the first image processing unit 132 applies a process of enhancing the printed character portion of the tablet to the tablet areas detected in step S3, and generates a pair of printed-character-enhanced images.

As described above, the illumination irregularity of the irradiating unit 126 and the shape irregularity of the tablet T often have low frequency bands compared to the printed character portion of the tablet T. Accordingly, the low-frequency components of the tablet areas are removed by the low-frequency component removing unit 134, and the printed-character-enhanced images are generated. The image $G_6$ shown in FIG. 3 is an example of the printed-character-enhanced image.

In step S5 (example of second image obtaining step, example of second image obtaining function), the imaging control unit 128 sequentially turns on, one by one, the first light source 104, the second light source 106, the third light source 108 and the fourth light source 110 disposed in the one side of the z-axis direction and turns off the other light sources to thereby sequentially switch the illumination direction in which the surface of the tablet T is irradiated, and causes the camera 120 to image the tablet T every time the illumination direction is switched. Accordingly, the obtaining unit 124 obtains four (example of at least three) taken images of the tablet T taken from the same point while differentiating the illumination directions of light to the upper surface of the tablet T.

The imaging control unit 128 sequentially turns on, one by one, the fifth light source 112, the sixth light source 114, the seventh light source 116 and the eighth light source 118 disposed in the other side of the z-axis direction and turns off the other light sources to thereby sequentially switch the illumination direction in which the tablet T is irradiated, and causes the camera 122 to image the tablet T every time the illumination direction switched. Accordingly, the obtaining unit 124 obtains four taken images of the tablet T taken from the same point while differentiating the illumination directions of light to the lower surface of the tablet T.

In step S6, the second image processing unit 136 detects tablet areas in each of which the tablet T is imaged, from the taken images obtained in step S5. Note that the tablet area of the upper surface and the tablet area of the lower surface of the same tablet are detected as a pair of tablet areas of the same tablet in association with each other.

In step S7 (example of second image processing step, example of second image processing function), the second image processing unit 136 applies a process of extracting only the engraved mark portion from a three-dimensional shape of the tablet to the tablet areas detected in step S6, and generates a pair of engraved-mark-extracted images.

Here, the three-dimensional information obtaining unit 138 obtains three-dimensional information using photometric stereo (photometric stereo method), and generates an xyz image (three-dimensional image).

The photometric stereo is a method of estimating a normal direction of a surface at each position by using multiple images taken at the same point while differentiating light emitting directions, based on variation in brightness at the corresponding position. That is, by the photometric stereo, it is possible to obtain a normal unit vector orthogonal to a tangent plane at each position.

Preferably, the four images taken by the camera 120 used for photometric stereo are respectively normalized by the second image processing unit 136 with an average of detected signal values of the tablet areas. This also applies to the four images taken by the camera 122. The first light source 104, the second light source 106, the third light source 108, the fourth light source 110, the fifth light source 112, the sixth light source 114, the seventh light source 116 and the eighth light source 118 of the irradiating unit 126 are respective bar-shaped light sources (bar illumination). By adjusting the average luminance in the tablet areas of the taken images, the constraint of "a point light source at infinity" that is a constraint in principle for use of photometric stereo is relaxed so that photometric stereo can be applied even under a bar illumination condition.

The curvature image generating unit 140 calculates a normal curvature from the normal unit vector (example of three-dimensional information) obtained by photometric stereo. The normal curvature is a curvature of a line of intersection (curved line) between a plane and a cut curved surface, the curved surface being cut by the plane along a normal direction. Here, the normal curvature is obtained over 360° about the normal unit vector as the axis in order to obtain the maximum principal curvature that is the maximum value of the normal curvature and the minimum principal curvature that is the minimum value thereof.

Next, the curvature image generating unit 140 calculates an average curvature. The average curvature can be obtained by (maximum principal curvature+minimum principal curvature)/2.

Furthermore, the curvature image generating unit 140 generates curvature images as the engraved-mark-extracted images, from the average curvature at each position calculated as described above. In this embodiment, the curvature images where a position having a relatively high average curvature is represented to have a relatively high luminance, are generated. Accordingly, it is possible to generate the engraved-mark-extracted images by extracting the engraved marks and representing the engraved marks with relatively high luminance.

Figure 8:
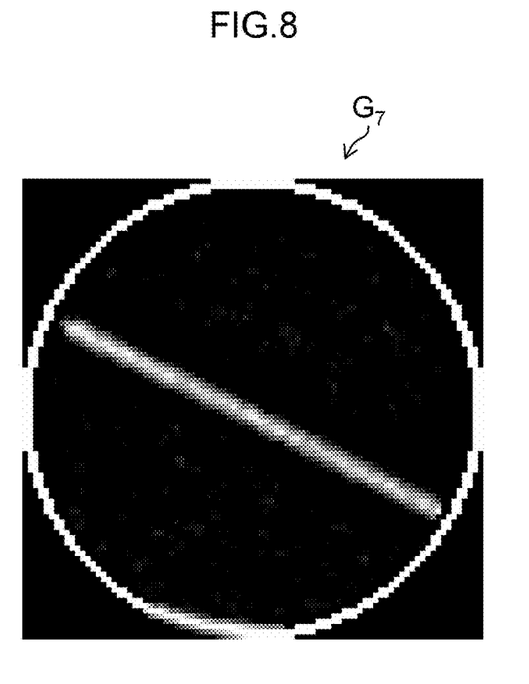
FIG. 8 shows an example of an engraved-mark-extracted image.

The image $G_7$ shown in FIG. 8 is an example of the engraved-mark-extracted image that is a result of applying the process of extracting only the engraved mark portion to the image $G_3$ show in FIG. 2. Here, the range of the z axis is adjusted.

In step S8 (example of difference image generating step, example of difference image generating function), the difference image generating unit 142 generates a pair of difference images obtained by subtracting the engraved-mark-extracted images generated in step S7 from the printed-character-enhanced images generated in step S4, for each tablet area.

Figure 9:
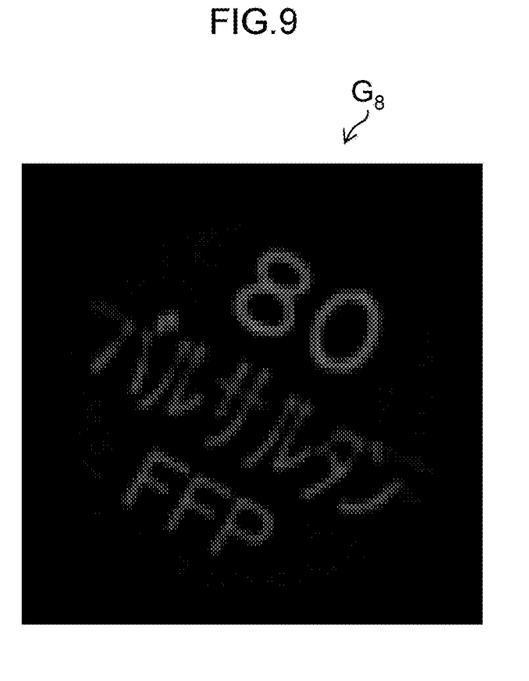
FIG. 9 shows an example of a difference image.

The image $G_8$ shown in FIG. 9 is an example of the difference image that is a result obtained by subtracting the image $G_7$ that is the engraved-mark-extracted image shown in FIG. 8 from the image $G_6$ that is the printed-character-enhanced image shown in FIG. 3. As described above, only the printed character portion is appropriately extracted as a portion having relatively high luminance. Note that no difference is taken on the contour portion of the tablet extracted in the image $G_7$.

In step S9, the image processing device 130 selects the difference images of the tablet. In a case where multiple tablets are placed on the stage 102, a pair of difference images are selected from among multiple pairs of difference images.

In step S10, a pair of master images of the dispensed medicine is read from the storage unit 148 and thus obtained. In a case where multiple medicines are dispensed, a pair of master images of one medicine among the dispensed medicines is read. The master image is an image where the printed character portion is represented as a portion having relatively high luminance.

In step S11, the determining unit 150 calculates similarity between the difference images selected in step S9 and the master images obtained in step S10. The similarity described here is calculated such that the higher the similarity property is, the higher the value of the similarity is. The similarity may be calculated by a publicly known method.

In step S12, the determining unit 150 determines whether the medicine described on the prescription is the same as the imaged medicine or not based on the similarity calculated in step S11. Here, the medicines are determined to be the same if the similarity is larger than a predetermined threshold.

In step S13, it is determined whether or not the difference images selected in step S9 have been collated with all the master images of the dispensed medicine. If there is any master image having not been collated yet, the processing returns to step S10, a new pair of master images is selected, and analogous processes are repeated. If all the master images have been collated, the processing transitions to step S14.

In step S14, it is determined whether collation of all the difference images generated in step S8 have been completed or not. If there is any difference image having been not collated yet, the processing returns to step S9, a new pair of difference images is selected, and analogous processes are performed. If all the difference images have been collated, the processing transitions to step S15.

In step S15, based on the collation result between the master image and the difference image, it is determined whether the dispensed medicine (medicines) conforms to the prescription or not.

If the dispensed medicine does not conform to the prescription, the processing transitions to step S16, the display unit 152 displays that the medicine described on the prescription is absent (error indication), and the processes of this flowchart are finished.

On the contrary, if the dispensed medicine conforms to the prescription, the processing transitions to step S17, the display unit 152 displays that the inspection result is normal (normal indication), and the processes of this flowchart are finished.

The similarities may be calculated for all the combinations of all the master images of the dispensed medicines and all the generated difference images, so that it may be determined that the medicine to be dispensed is the same as the dispensed medicine, for a combination having the highest similarity.

In this case, the combination where the medicine to be dispensed is determined to be the same as the dispensed medicine may be sequentially removed from collation targets. The combination having the highest similarity among the combinations of the remaining master images and the remaining difference images may be determined that the medicine to be dispensed is the same as the dispensed medicine.

[Setting Region of Interest]

If the entire tablet area is adopted as a region of interest, the states of images are different even on the same tablet between a case where the tablet is placed at a center (a position close to the optical axes of the camera 120 and the camera 122) of the stage 102 and a case where the tablet is placed at an end (a position relatively distant from the optical axes of the camera 120 and the camera 122), unless imaging is performed through a telecentric optical system. For example, if the tablet is placed at an end of the stage 102, the average curvature obtained by photometric stereo includes information on the side surface of the tablet.

Accordingly, it is preferable that the region of interest be set on the tablet. As to the region of interest, a position, shape and size of the region of interest may be set in consideration of the tablet placing position. For example, the determining unit 150 (example of region-of-interest setting unit) sets the regions of interest in the images of the tablet medicines.

Figure 10:
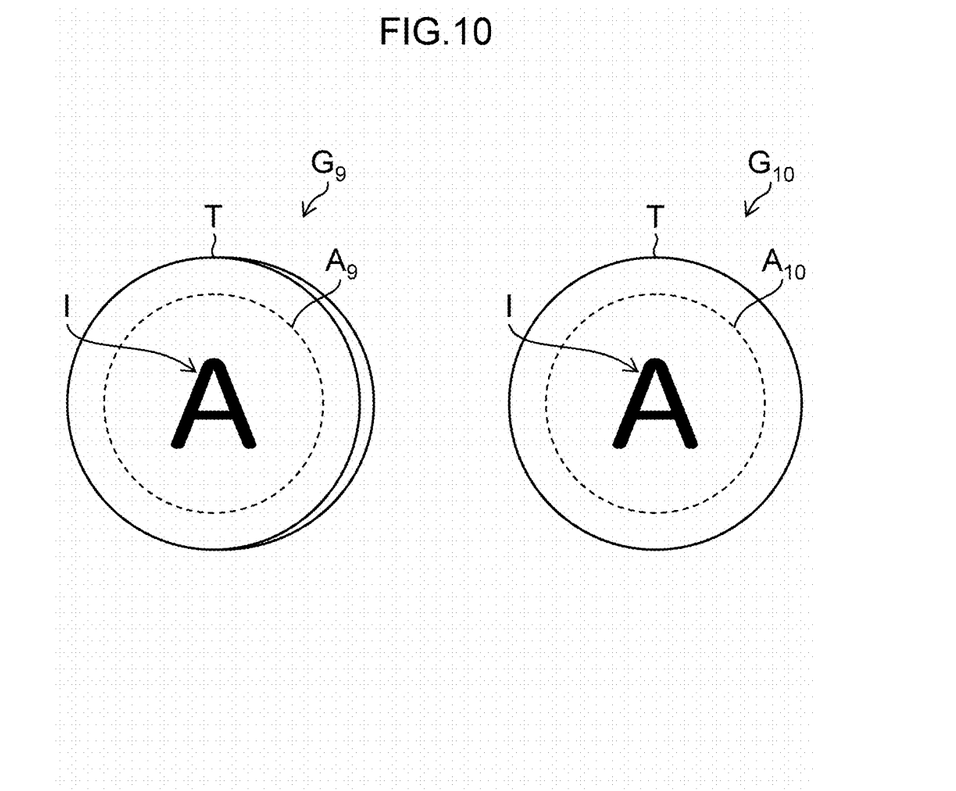
FIG. 10 shows examples of a difference image of a tablet and a region of interest.

The image $G_9$ shown in FIG. 10 is an example of a difference image of the tablet placed at an end of the stage 102. The image $G_{10}$ shown in FIG. 10 is an example of a difference image of the tablet placed at a center of the stage 102. As shown in FIG. 10, a region of interest $A_9$ is set in the image $G_9$, and a region of interest $A_{10}$ is set in the image $G_{10}$.

Further, the determining unit 150 (example of template generating unit) generates a templates from the master images in conformity with the positions, shapes and sizes of the set regions of interest, and collates the regions of interest in the difference images with the templates.

By setting the regions of interest as described above, the collation accuracy can be improved.

Figure 11:
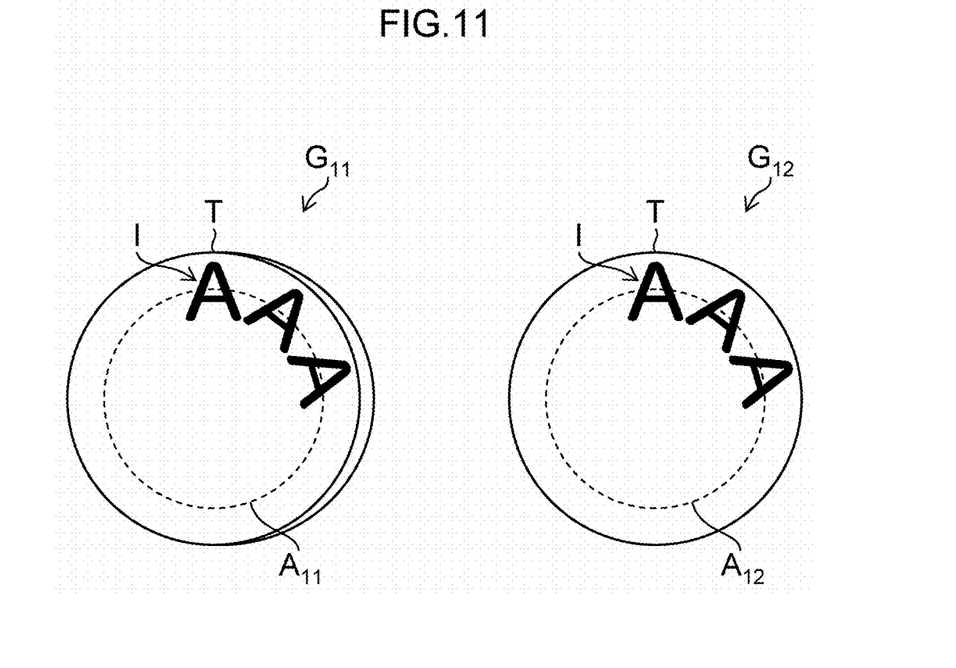
FIG. 11 shows an example of a difference image of a tablet and a region of interest.

The image $G_{11}$ shown in FIG. 11 is an example of a difference image of the tablet placed at an end of the stage 102. The image $G_{12}$ shown in FIG. 11 is an example of a difference image of the tablet placed at a center of the stage 102. As shown in FIG. 11, a region of interest $A_{11}$ is set in the image $G_{11}$, and a region of interest $A_{12}$ is set in the image $G_{12}$.

In this tablet, a printed character portion or an engraved mark portion is disposed along the circumference of the tablet. Accordingly, the printed character portion or the engraved mark portion is not confined within the region of interest $A_{11}$ and the region of interest $A_{12}$. As described above, if the region of interest is set at a center of the tablet, collation accuracy is reduced in some cases. Accordingly, the region of interest may be set at a different position for each tablet.

[Other]

The image processing method described above can be configured as a program of causing a computer to achieve the first image obtaining function, the first image processing function, the second image obtaining function, the second image processing function and the difference image generating function, and configured as a non-transitory recording medium, such as a CD-ROM (Compact Disk-Read Only Memory), storing the program.

In the thus described embodiments, for example, the hardware structure of the processing unit that executes various types of processes such as of the image processing device 130, the prescription information obtaining unit 144, the master image obtaining unit 146 and the determining unit 150, is any of various processors as described below. The various processors include: a CPU (Central Processing Unit), which is a general-purpose processor executing software (program) to function as various processing units; a programmable logic device (PLD), such as an FPGA (Field Programmable Gate Array), which is a processor whose circuit configuration can be changed after production; and circuitry, such as an ASIC (Application Specific Integrated Circuit), which has a circuit configuration designed in a dedicated manner to execute a specific process.

One processing unit may be configured by any one of these various processors, or configured by the same type or different types of two or more processors (e.g., multiple FPGAs or a combination of a CPU and an FPGA) among these various processors. Alternatively, multiple processing units may be made up of a single processor. Examples where multiple processing units are made up of a single processor include, firstly, a mode where as typified by a computer, such as a server and a client, a combination of one or more CPUs and software constitutes a single processor, and the processor functions as multiple processing units. Secondly, as typified by a system on chip (SoC), the examples include a mode of using a processor where the function of the entire system including multiple processing units is achieved by a single IC (Integrated Circuit) chip. As described above, various processing units are configured using one or more various processors as a hardware configuration.

Furthermore, more specifically, each of the hardware structures of these various processors is circuitry including combined circuit elements, such as semiconductor elements.

The technical scope of the present invention is not limited to the scope described in the above embodiments. The configurations and the like in the respective embodiments can be appropriately combined between the embodiments in a range without departing from the spirit of the present invention.

REFERENCE SIGNS LIST

100 Medicine inspection device
102 Stage
102A Mounting surface
102B Rear surface
104 First light source
106 Second light source
108 Third light source
110 Fourth light source
112 Fifth light source
114 Sixth light source
116 Seventh light source
118 Eighth light source
120 Camera
122 Camera
124 Obtaining unit
126 Irradiating unit
128 Imaging control unit
130 Image processing device
132 First image processing unit
134 Low-frequency component removing unit
136 Second image processing unit
138 Three-dimensional information obtaining unit
140 Curvature image generating unit
142 Difference image generating unit
144 Prescription information obtaining unit
146 Master image obtaining unit
148 Storage unit
150 Determining unit
152 Display unit
A9 to A12 Region of interest
G1 to G12 Image
I Identification information
T Tablet
S1 to S17 Processes of image processing method

What is claimed is:

1. An image processing device, comprising a processor configured to:
obtain at least one taken image of a medicine, the taken image being taken with a surface of the medicine being irradiated with light;
perform a process of enhancing a printed character portion of the medicine based on the at least one taken image, and generate a printed-character-enhanced image;
obtain at least three taken images of the medicine, the images being taken with illumination directions of light to the surface of the medicine different from each other;
perform a process of extracting only an engraved mark portion from a three-dimensional image of the medicine based on the at least three taken images, and generate an engraved-mark-extracted image; and
generate a difference image between the printed-character-enhanced image and the engraved-mark-extracted image.

2. The image processing device according to claim 1, wherein the processor is further configured to:
obtain three-dimensional information on the surface of the medicine by photometric stereo based on the at least three taken images; and
generate a curvature image that represents a curvature of a local area of the surface of the medicine based on the obtained three-dimensional information,
wherein the generated curvature image is adopted as the engraved-mark-extracted image.

3. The image processing device according to claim 1, wherein the processor is further configured to perform a process of removing a low-frequency component from the at least one taken image.

4. A medicine inspection device, comprising:
a stage on which a medicine is placed;
an irradiating unit configured to include at least three light sources that irradiate a surface of the medicine placed on the stage, with light in a plurality of illumination directions different from each other;
an imager configured to image the medicine; and
a processor configured to:
control the irradiating unit and the imager to obtain at least one taken image of the medicine, the image being taken with irradiating the surface of the medicine with light;
perform a process of enhancing a printed character portion of the medicine based on the at least one taken image, and generate a printed-character-enhanced image;
control the irradiating unit and the imager to obtain at least three taken images of the medicine, the images being taken with illumination directions of the light to the surface of the medicine different from each other;
perform a process of extracting only an engraved mark portion from a three-dimensional image of the medicine based on the at least three taken images, and generate an engraved-mark-extracted image; and
generate a difference image between the printed-character-enhanced image and the engraved-mark-extracted image.

5. The medicine inspection device according to claim 4, wherein the processor is further configured to:
obtain prescription information;
obtain a master image of a medicine to be dispensed based on the prescription information; and
collate the master image with the generated difference image, and determine whether or not the medicine to be dispensed is identical to the medicine placed on the stage.

6. The medicine inspection device according to claim 5, wherein the processor is further configured to:
set a region of interest in an image of the medicine;
generate a template from the master image in conformity with the set region of interest; and
collate the region of interest of the difference image with the template.

7. The medicine inspection device according to claim 4, wherein a plurality of medicines packaged into a divided bag are placed on the stage.

8. The medicine inspection device according to claim 4, wherein the irradiating unit comprises a first light source configured to emit light in a first direction, a second light source configured to emit light in a second direction, a third light source configured to emit light in a third direction, and a fourth light source configured to emit light in a fourth direction, and
the second direction is a direction opposite to the first direction in plan view of the surface, the third direction is a direction orthogonal to the first direction in plan view of the surface, and the fourth direction is a direction opposite to the third direction in plan view of the surface.

9. The medicine inspection device according to claim 8, wherein the processor is further configured to cause the first light source, the second light source, the third light source and the fourth light source to irradiate the surface of the medicine with light.

10. An image processing method, comprising:
   a first image obtaining step of obtaining at least one taken image of a medicine, the taken image being taken with a surface of the medicine being irradiated with light;
   a first image processing step of performing a process of enhancing a printed character portion of the medicine based on the at least one taken image, and generate a printed-character-enhanced image;
   a second image obtaining step of obtaining at least three taken images of the medicine, the images being taken with illumination directions of the light to the surface of the medicine different from each other;
   a second image processing step of performing a process of extracting only an engraved mark portion from a three-dimensional image of the medicine based on the at least three taken images, and generating an engraved-mark-extracted image; and
   a difference image generating step of generating a difference image between the printed-character-enhanced image and the engraved-mark-extracted image.

11. A non-transitory and computer-readable recording medium wherein when an instruction stored in the recording medium is read by a computer, the instruction causes the computer to execute:
   a first image obtaining function of obtaining at least one taken image of a medicine, the taken image being taken with a surface of the medicine being irradiated with light;
   a first image processing function of performing a process of enhancing a printed character portion of the medicine based on the at least one taken image, and generate a printed-character-enhanced image;
   a second image obtaining function of obtaining at least three taken images of the medicine, the images being taken with illumination directions of the light to the surface of the medicine different from each other;
   a second image processing function of performing a process of extracting only an engraved mark portion from a three-dimensional image of the medicine based on the at least three taken images, and generating an engraved-mark-extracted image; and
   a difference image generating function of generating a difference image between the printed-character-enhanced image and the engraved-mark-extracted image.

* * * * *